(12) United States Patent
Yoon

(10) Patent No.: US 8,323,022 B2
(45) Date of Patent: Dec. 4, 2012

(54) INSTANT DENTAL BRIDGE

(76) Inventor: Han Seok Yoon, Seoul (KR)

( * ) Notice: Subject to any disclaimer, the term of this patent is extended or adjusted under 35 U.S.C. 154(b) by 11 days.

(21) Appl. No.: 12/991,555

(22) PCT Filed: Feb. 25, 2009

(86) PCT No.: PCT/KR2009/000888
§ 371 (c)(1),
(2), (4) Date: Nov. 8, 2010

(87) PCT Pub. No.: WO2009/145409
PCT Pub. Date: Dec. 3, 2009

(65) Prior Publication Data
US 2011/0091838 A1    Apr. 21, 2011

(30) Foreign Application Priority Data

May 26, 2008    (KR) .................. 10-2008-0048538

(51) Int. Cl.
*A61C 13/275* (2006.01)
(52) U.S. Cl. ........................................ 433/172; 433/191
(58) Field of Classification Search .......... 433/167–172, 433/181–182, 190–193, 174, 173, 175–176, 433/201.1, 202.1; 623/16.11
See application file for complete search history.

(56) References Cited

U.S. PATENT DOCUMENTS

| 4,790,754 A * | 12/1988 | Weissman ...................... 433/182 |
| 4,875,856 A * | 10/1989 | Grussmark ...................... 433/18 |
| 5,842,864 A * | 12/1998 | Unger ........................... 433/172 |
| 2005/0019720 A1 | 1/2005 | Harima et al. |
| 2006/0040234 A1 * | 2/2006 | Posca ........................... 433/177 |

FOREIGN PATENT DOCUMENTS

| KR | 20-0362484 | 9/2004 |
| KR | 20-0183838 | 3/2005 |
| KR | 10-2007-0117751 | 12/2007 |

OTHER PUBLICATIONS

International Search Report dated Aug. 31, 2009 from PCT/KR2009/000888.

\* cited by examiner

*Primary Examiner* — Cris L Rodriguez
*Assistant Examiner* — Matthew Seward
(74) *Attorney, Agent, or Firm* — Young & Thompson

(57) ABSTRACT

The instant dental bridge is one used in surgical operations in areas of missing teeth between abutment teeth includes: an artificial tooth or teeth (2) formed with slots (6) in recessed parts near to the gum; a connecting body (1) which has through holes (3) formed in positions corresponding to the slots (6) and projections joined onto the abutment teeth, and of which the entire surface, except the surfaces (5') in contact with the abutment teeth, is covered by the artificial tooth (2) or by the same material as the artificial tooth; and wires (8) for securing the abutment teeth and the connecting body (1) to each other, by being wound through gaps (7) neighboring the abutment teeth and through the slots (6) and the through holes (3).

4 Claims, 5 Drawing Sheets

INSTANT DENTAL BRIDGE

CROSS-REFERENCE TO RELATED APPLICATIONS

This application is a National Stage entry from PCT application number PCT/KR2009/000888 filed Feb. 25, 2009 and claims benefit for foreign priority from KR Application Number 10-2008-0048538 filed May 26, 2008.

TECHNICAL FIELD

The present invention relates to an instant dental bridge which allows immediacy in tooth-extraction and which, if there is a poor state of contact between the dental bridge and the soft tissue of the missing tooth (teeth) due to changes in the soft tissue over time following the operation, allows the dental bridge to be immediately removed from its position and then readjusted to a position where the state of contact with the soft tissue is improved, and allows the removed dental bridge to be reused.

BACKGROUND ART

Teeth have the function of masticating and pronouncing and also provide aesthetic impression of a human. Therefore, missing teeth cause much inconvenience in masticating food and pronouncing words, and have a detrimental effect on the appearance of a person. So, when permanent teeth are missing, it is needed to restore the function of the teeth through prosthesis treatment.

Generally, a dental bridge means a fixed bridge including artificial teeth, and can be classified, depending on the number of missing teeth, as a fixed dental bridge which is used when one or two teeth are missing, a removable partial dental bridge (so called partial denture) which is used when much more teeth are missing, and a full denture which is used when whole teeth are missing.

Generally, a fixed dental bridge is operated by covering on both of abutment teeth a cap made with the same shape as the shape of the abutment teeth on both sides of the missing teeth, in which the impression should be obtained after reduce the upper and side area of the abutment teeth to the size of ⅔ of original size. These operating methods, however, can damage the teeth nerve while reduce natural teeth, causing severe pain to the patient during the operation. Also, when used for a long time, there has been problem that holes are generated on the occlusal of crown surface (masticating surface) damaging pulp or generating dental caries and produce critical damage to the natural teeth.

Meanwhile, one method of operating implant to solve the previous problems is to bury an implant in spiral forms in the bone and suture the soft tissue, which has the problem of waiting a long time until the tissues are recovered making the time of treatment longer. Also, it takes 2 months to a year for the implant and bone tissue to be completely combined, depending on the bone quality, making patients suffer from various inconvenience and pain. By using the instant dental bridge of the present invention, however, the instant dental bridge can be immediately installed between the abutment teeth after finishing implant operation, and since the recess into which the cover screw of implant can be inserted is still formed on the lower part of the instant dental bridge (bottom surface of the support), abutment teeth and implant are securely protected until the implant prosthesis is completed and the patient can use the instant dental bridge with little inconvenience.

DISCLOSURE OF INVENTION

Object of the Invention

The present invention aims to provide dental bridge by which operation can be carried out with simple procedure and low cost, the dental bridge can be removed at any time enabling early treatment of gum or dental caries easily, the reduction of abutment teeth is minimized thereby suppressing the possibility of dental caries, and when the pontic do not contact well with the soft tissue of missing teeth due to the change of the soft tissue over time after the operation, the dental bridge can be immediately removed and adjusted to improve the state of contact with soft tissue. In other words, the dental bridge of the present invention can be reused.

Also, the present invention aims to provide dental bridge that can be conveniently used for a certain period until implant prosthesis is completed when the implant is buried in the missing teeth area.

Finally, the present invention aims to provide dental bridge that can restore the function of masticating and pronouncing, and aesthetic impression, and prevent the movement of abutment teeth and elongation of opposite teeth.

SUMMARY OF INVENTION

In order to achieve the object of the present invention, the instant dental bridge according to the present invention, as described in claim 1, which is operated at a missing teeth area between abutment teeth, is characterized in that comprises an artificial teeth with slots formed in recessed area near to the gum; a support which comprises through holes formed in positions corresponding to the slots and projections joined onto the abutment teeth, and of which the entire surface, except the surfaces in contact with the abutment teeth, is covered by the artificial tooth or by the same material as the artificial tooth; and wires for securing the abutment teeth and the support to each other, by being wound through inter dental spaces neighbouring the abutment teeth and through the slots and the through holes.

Also the instant dental bridge of the present invention as described in claim 2 is characterized in that a recess is further formed in the bottom surface of the support.

Also, the instant dental bridge of the present invention as described in claim 3 is characterized in that a fixing pin is further formed at the surface of the support combined with artificial teeth.

Also, the instant dental bridge of the present invention as described in claim 4 is characterized in that the bottom surface of the support is covered with the same material as the material of the artificial teeth.

Advantageous Effects

According to the present invention, the reduction amount of the abutment teeth which is inevitable when fixing the dental bridge to abutment teeth can be greatly reduced, thereby effectively protecting abutment teeth. Therefore, erosion of the abutment teeth by other material can be prevented and little chance of dental caries.

Also, according to the present invention, the separation of the dental bridge from abutment teeth when masticating food after operation of the dental bridge is completely prevented by the occlusal rest and wire.

Also, according to the present invention, the process of operating fixed dental bridge becomes simpler, thereby reducing the cost of operating.

DESCRIPTION OF THE NUMERALS IN THE DRAWING

Figure 1:
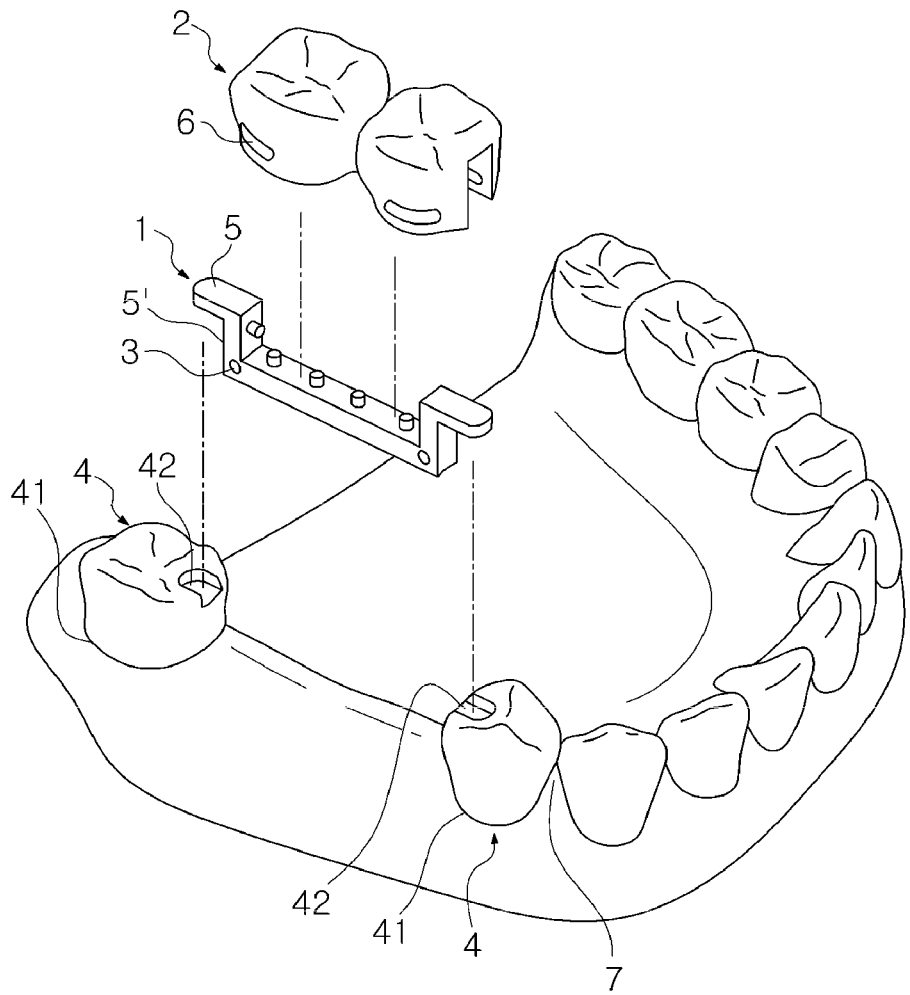
FIG. 1 is a perspective view showing the state where the instant dental bridge according to one embodiment of the present invention is separated in oral cavity.

1 . . . support
1' . . . fixing pin
2 . . . artificial teeth
3 . . . through hole
4 . . . abutment teeth
41 . . . cervical area
42 . . . rest seat
5 . . . occlusal rest
5' . . . contacting area
6 . . . slot
7 . . . interdental space
8 . . . wire
9 . . . implant
10 . . . recess
11 . . . cover screw
12 . . . buccal lug
13 . . . lingual lug

MODES FOR CARRYING OUT THE INVENTION

The instant dental bridge of the present invention will now be further described with reference to the drawings attached.

Figure 2:
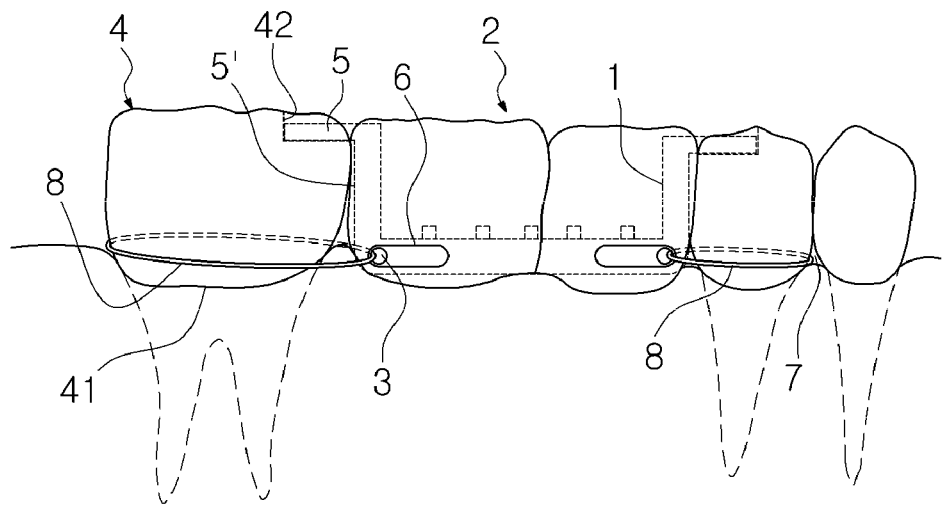
FIG. 2 illustrates the state where the instant dental bridge according to one embodiment of the present invention is operated at the missing teeth area.
Figure 3:
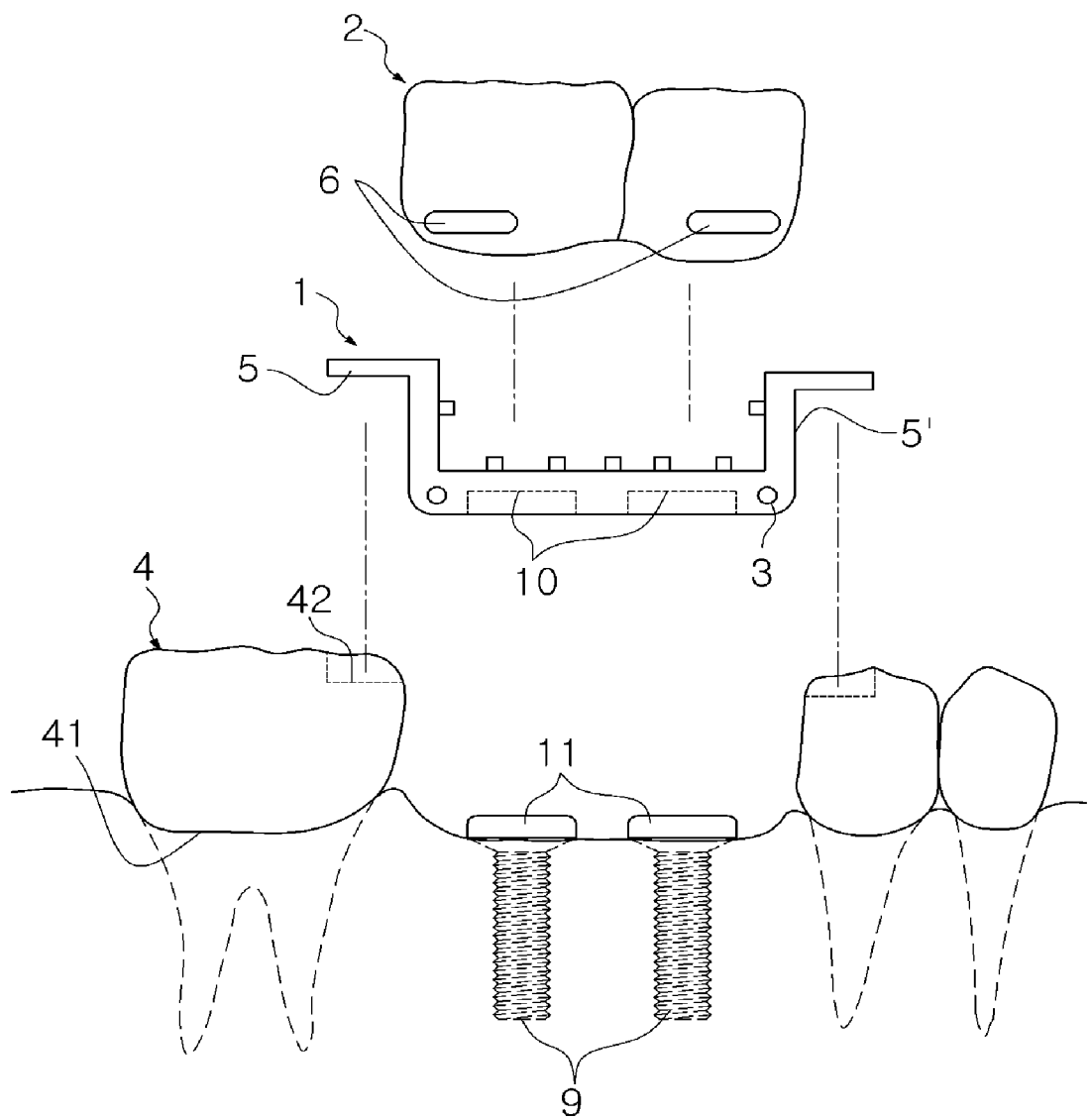
FIG. 3 illustrates the state where the instant dental bridge according to another embodiment of the present invention is separated in oral cavity, with implant being operated at the missing teeth area.
Figure 4:
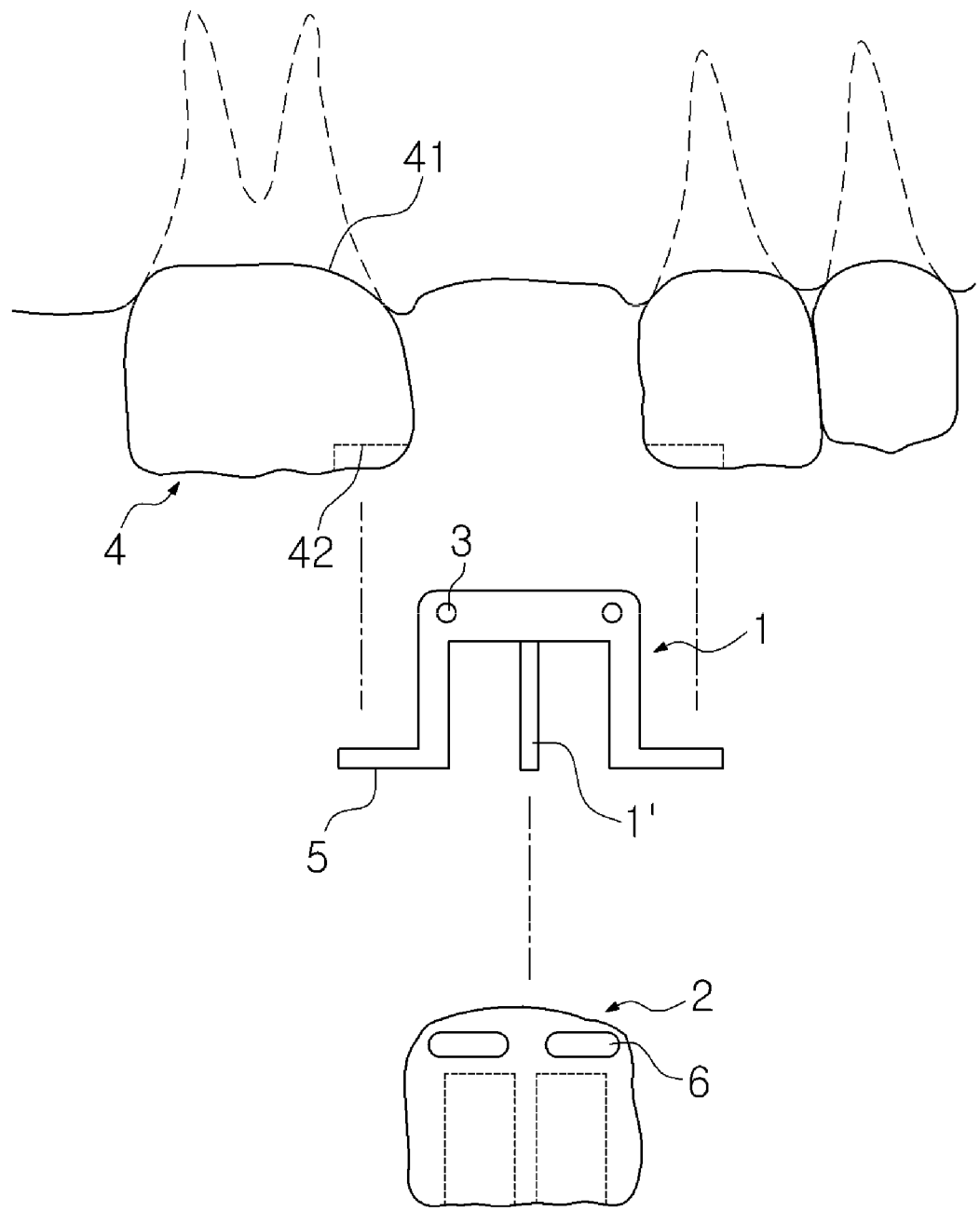
FIG. 4 illustrates the state where the instant dental bridge according to another embodiment of the present invention is separated in oral cavity, with the operated area being at the upper jaw.
Figure 5:
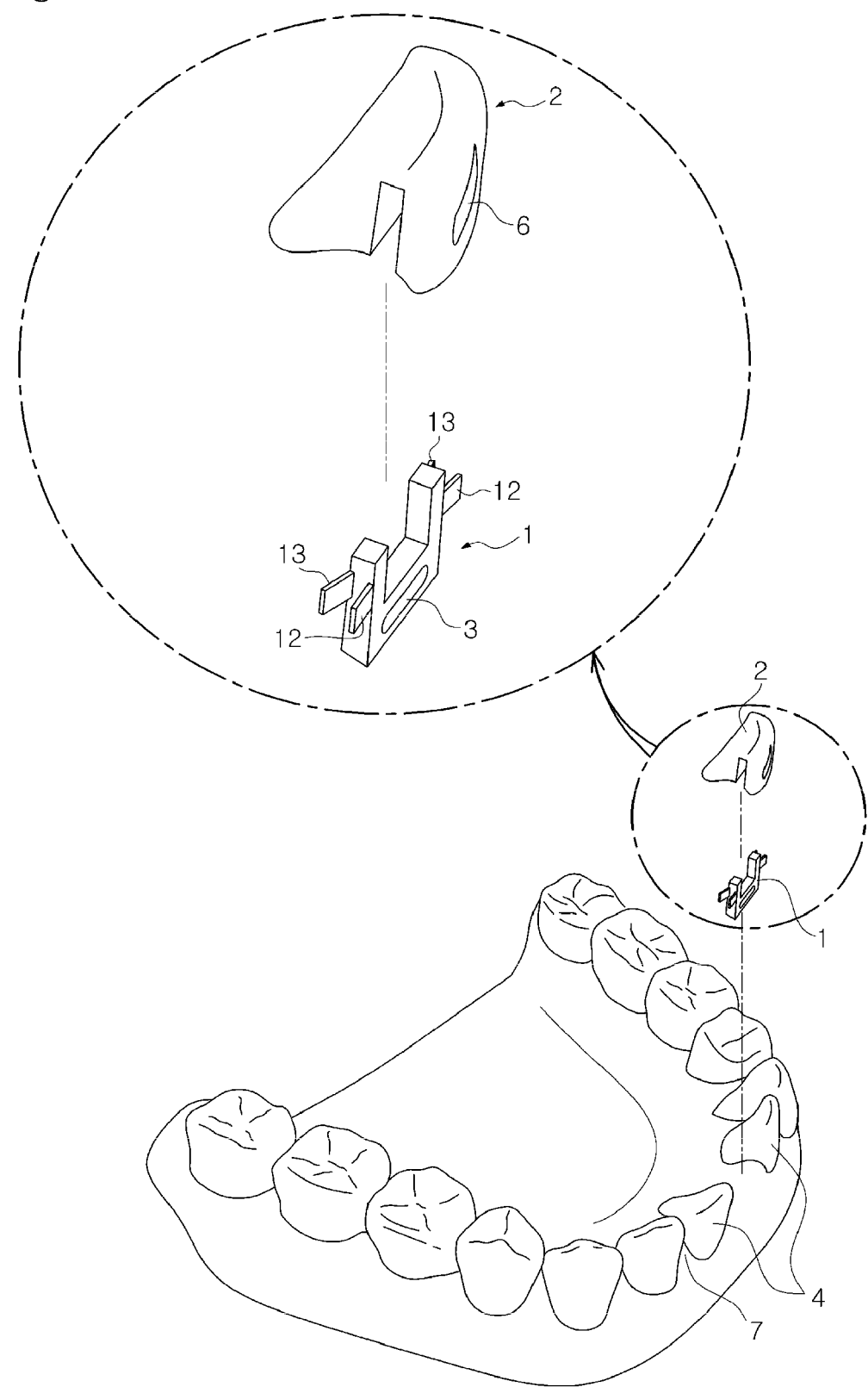
FIG. 5 illustrates the state where the instant dental bridge according to another embodiment of the present invention is separated in oral cavity, with the operated area being at the anterior teeth.
Figure 6:
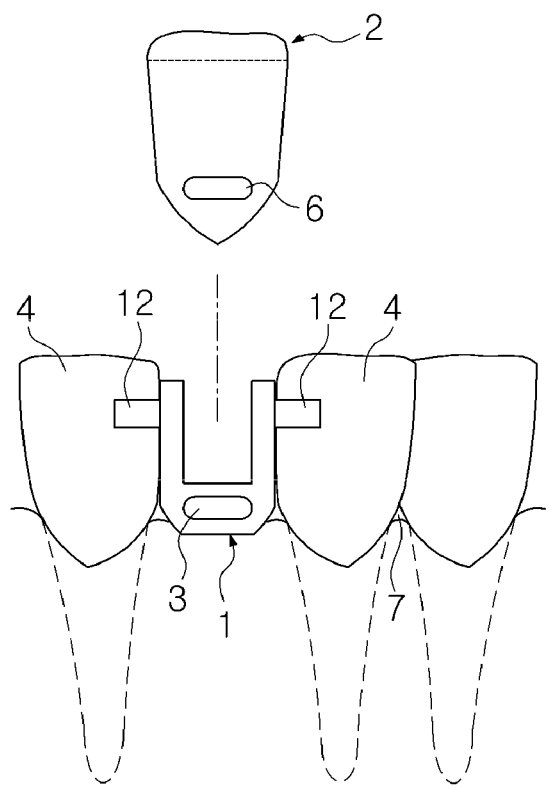
FIG. 6 is a front view showing the instant dental bridge shown in FIG. 5 is inserted in the missing teeth area before using the wire.
Figure 7:
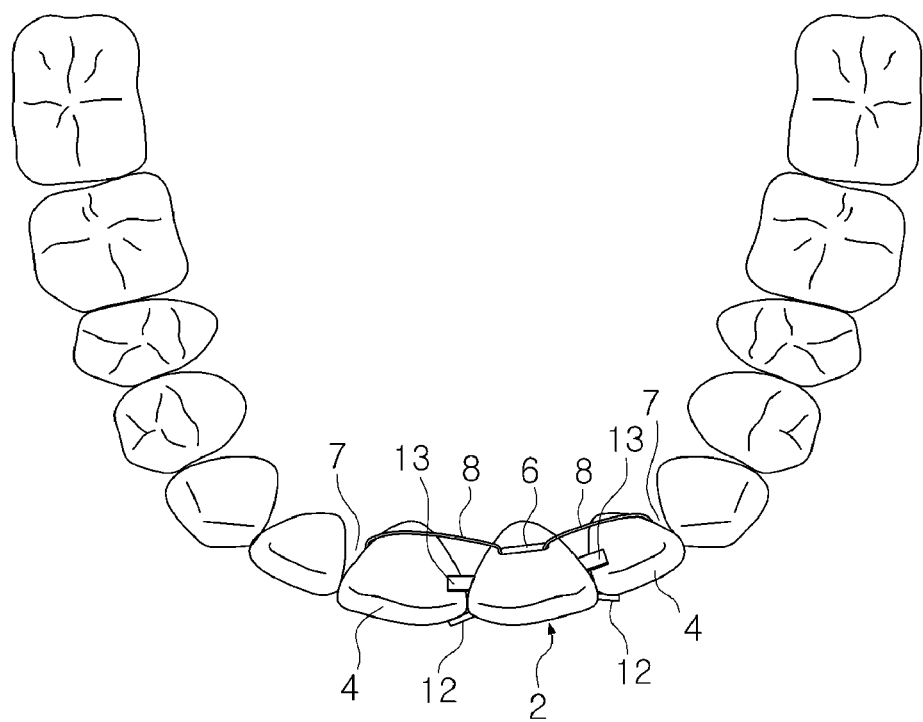
FIG. 7 is a plane view of FIG. 6 after wire is used.

In the drawings attached, FIG. 1 is a perspective view showing the state where the instant dental bridge according to one embodiment of the present invention is separated, FIG. 2 illustrates the state where the instant dental bridge according to one embodiment of the present invention is operated at the missing teeth area, FIG. 3 illustrates the state where the instant dental bridge according to another embodiment of the present invention is separated in oral cavity, with implant operated being at the missing teeth area, FIG. 4 illustrates the state where the instant dental bridge according to another embodiment of the present invention is separated in oral cavity, with the operated area being at the upper jaw, FIG. 5 illustrates the state where the instant dental bridge according to another embodiment of the present invention is separated in oral cavity, with the operated area being at the anterior teeth, FIG. 6 is a front view showing the instant dental bridge shown in FIG. 5 is inserted in the missing teeth area before using the wire, and FIG. 7 is a plane view of FIG. 6 after wire is used.

As shown in the figures, the instant dental bridge of the present invention comprises a support 1, artificial teeth 2 and a wire 8.

Among them, the support 1 is made of metal, and the entire side surface of the support 1 is covered by the recess area of the artificial teeth 2 except the area 5' contacting both of the abutment teeth 4.

In FIGS. 1 and 2, one side contact area 5' of each support 1 is contacted to both of the abutment teeth 4 which are located at right and left sides of the missing teeth area, and a through hole 3 is formed on each of the two lower sides of the support.

The through holes 3, although not clearly shown in FIGS. 1 and 2, are arranged in parallel one another. Also, occlusal rest 5 is formed on each two upper portion of the support 1 in the form of protrusion in the direction of the two abutment teeth 4.

The occlusal rest 5 is closely contacted by resting inside the rest seat 42 which has been prepared in the form of hollow space in the occlusal area on both of the abutment teeth 4. In this way, the upper surface of the occlusal rest 5 coincides with the occlusal surface of the abutment teeth 4. As a result, when occlusal stress is applied to the artificial teeth 2 including the support 1, collapse of the artificial teeth to the direction of the gum is prevented through the counter reaction of the occlusal rest 5 rested on the rest seat 42. At this state, one end of the wire 8 is inserted into the slot 6 of the artificial teeth 2 and the through hole 3 of the support 1 penetrating the teeth, and then the end of the wire is penetrated through the interdental space 7 along the cervical area 41 of the abutment teeth 4 and protruded to the buccal. Then, one end of the wire protruded to the buccal is combined to the other end of the wire by ligature, unnecessary parts are cut and the rest is bent into the slot 6. Then, the empty space of the slot 6 is completely filled with self curing resin or composite resin so that the ligature portion of the wire which is bent into the slot 6 is not loosened. Then, by filling the lower portion of the support 1 with the same material as that of the artificial teeth 2, the dental bridge of the present invention is closely contacted with the gum (gingiva). Hence, in the dental bridge of the present invention, the artificial teeth 2 are not separated from the support 1.

FIG. 3 shows another embodiment of the present invention, and illustrates the state where the instant dental bridge of the present invention is operated after the implant 9 is buried at the teeth missing area between abutment teeth. As well shown in the figure, a recess 10 is further formed at lower surface of the support 1 so that the cover screw 11 which is installed on the upper part of the implant and exposed outside the gum can be received. In this case, the support 1 and both the abutment teeth 4 inside the artificial teeth 2 are fixed by the wire 8.

FIG. 4 shows the case where the instant dental bridge of the present invention is installed at the upper jaw, which is the same as the above-mentioned embodiment except that one or more of fixing pin 1' is installed on the surface of the support 1 in order to increase the combination between the artificial teeth 2 and support 1. Here, the fixing pin 1' needs not to be the same as that shown in FIG. 4 and any other types of pin can be used. FIGS. 5 to 7 illustrate other embodiments of the instant dental bridge of the present invention, and in case the mesio-distal diameter at the six anterior teeth of the missing teeth in lower or upper jaws has narrow width, the through hole 3 of the artificial teeth 2 and the slot 6 completely coincides. And, in the above case, the buccal lug 12 and lingual lug 13 protruded from the support (1) are closely contacted to both of the abutment teeth (4) thereby fixing the position of the support (1).

Meanwhile, it should be noticed that the previous examples are not intended to limit the invention and that the present invention can be carried out with various modification by those skilled in the art.

Industrial Applicability

According to the present invention, the dental bridge can be removed any time when needed thereby making it possible to treat preventive procedure such as gum treatment or dental caries and extending the lifetime of the artificial teeth longer than prior art dental bridges. Also, since the dental bridge of the present invention can be operated immediately after extraction, the function of teeth like masticating and pronouncing is quickly restored thereby reducing inconvenience in everyday life. Also, since there is little need of cutting out the area of abutment teeth where the dental bridge is operated or the amount of cutting is very small even when cutting is needed, the teeth nerve is not damaged thereby preventing excessive reaction of the teeth nerve to external stimulation such as cool or hot water.

What is claimed is:

1. An instant temporary dental bridge, comprising:
   a support (1) for locating between abutment teeth (4) where one or two teeth are missing, the support comprising i) a through hole (3) formed on a lower side of the support (1), ii) a resting element (5, 12, 13) located at both ends of the support (1), iii) a recess (10) formed in a bottom surface of the support (1), and iv) projections from both ends of the support (1) and occlusal rest elements (5), the occlusal rest elements configured to rest on a top surface of a rest seat (42) formed in the abutment teeth (4);
   a screw (11) with an implant portion (9),
   wherein, in assembling the dental bridge, the recess (10) is inserted over the screw (11) and configured to protect the implant portion (9) by covering and accommodating, within the recess (10), a part of the screw (11) revealed outside of the gums;
   one or two artificial teeth (2) for situating on the support (1), the artificial teeth (2) each comprising a slot (6) formed on a lower side of the artificial tooth (2) at a location corresponding to, and aligned with, the through hole (3), the slot extending through the tooth (2) and exposed to an outer surface of a front and a rear of the tooth (2),
   wherein, in assembling the dental bridge, an entire surface of the support (1) is covered by the artificial teeth (2) or by a same material as a material of the artificial teeth (2); and
   a wire (8) for temporarily securing the abutment teeth (4), the artificial teeth (2), and the support (1) to each other by being wound through an interdental space (7) neighbouring the abutment teeth (4) and through the slot (6) and the through hole (3).

2. The instant dental bridge of claim 1, wherein, at each end of the support (1), the occlusal rest elements (5) comprising a pair of spaced apart projecting elements defining a buccal lug (12) and a lingual lug (13).

3. An instant temporary dental bridge, comprising:
   a support (1) for locating between abutment teeth (4) where one or two teeth are missing, the support comprising i) a through hole (3) formed on a lower side of the support (1), ii) a resting element (5, 12, 13) located at both ends of the support (1), and iii) a recess (10) formed in a bottom surface of the support (1);
   a screw (11) with an implant portion (9),
   wherein, in assembling the dental bridge, the recess (10) is inserted over the screw (11) and configured to protect the implant portion (9) by covering and accommodating, within the recess (10), a part of the screw (11) revealed outside of the gums;
   one or two artificial teeth (2) for situating on the support (1), the artificial teeth (2) each comprising a slot (6) formed on a lower side of the artificial tooth (2) at a location corresponding to, and aligned with, the through hole (3), the slot extending through the tooth (2) and exposed to an outer surface of a front and a rear of the tooth (2),
   wherein, in assembling the dental bridge, an entire surface of the support (1) is covered by the artificial teeth (2) or by a same material as a material of the artificial teeth (2); and
   a wire (8) for temporarily securing the abutment teeth (4), the artificial teeth (2), and the support (1) to each other by being wound through an interdental space (7) neighbouring the abutment teeth (4) and through the slot (6) and the through hole (3),
   the support (1) further comprising one or more fixing pins (1') located on the surface of the support (1) for insertion into a corresponding opening of the artificial tooth (2).

4. An instant temporary dental bridge, comprising:
   an implant screw, when implanted in a jaw, has an implanted portion (9) and an exposed portion (11) above the gum;
   a support (1) comprising i) a bottom element, a recess (10), ii) projections located at both ends of the support (1) extending from the bottom element, the projections comprising occlusal rest elements (5) located at both ends of the projections and a pair of spaced apart projecting elements defining a buccal lug (12) and a lingual lug (13), iii) through holes (3) located at both ends of the bottom element where the projections extending from, the through holes (3) running from front to back of the bottom element, and iv) one or more fixing pins (1') located on the surface of the support (1) for insertion;
   one or two artificial teeth (2) for mounting on the support (1), the artificial teeth (2) each comprising a side opening for fitting over one end of the projections and a slot (6) running from front to back of the artificial tooth (2); and
   a wire (8) for securing abutment teeth (4) and the support (1) to each other,
   wherein, in assembling the dental bridge, the recess (10) is inserted between the abutment teeth (4) to protect the implant screw by covering the exposed portion (11) outside of the gum,
   wherein, in assembling the dental bridge, the rest occlusal rest elements (5) are configured to rest on a top surface of a rest seat (42) formed in the abutment teeth (4),
   wherein, in assembling the dental bridge, the fixing pin (1') is inserted into a corresponding opening of the artificial tooth (2),
   wherein, in assembling the dental bridge, the support (1) is covered by the artificial tooth (2) or by same material as a material of the artificial tooth (2), and
   wherein, in assembling the dental bridge, the wire (8) is wound through an interdental space (7) neighbouring the abutment teeth (4) and through the slot (6) and the through hole (3) thereby temporarily securing the artificial tooth to the support and to the abutment teeth.

* * * * *